(12) United States Patent
Druk

(10) Patent No.: US 6,304,519 B1
(45) Date of Patent: Oct. 16, 2001

(54) METHOD AND APPARATUS FOR MEASURING SUBJECTIVE TIME

(76) Inventor: Vladimir Druk, 6555 Broadway, Apt. 1F, Riverdale, NY (US) 10471

(*) Notice: Subject to any disclaimer, the term of this patent is extended or adjusted under 35 U.S.C. 154(b) by 0 days.

(21) Appl. No.: 09/565,792

(22) Filed: May 5, 2000

(51) Int. Cl.[7] .............................. G04F 10/00; G04F 8/00
(52) U.S. Cl. .......................................................... 368/107
(58) Field of Search ................................. 368/10, 41.43, 368/107, 110–113

(56) References Cited

U.S. PATENT DOCUMENTS

| | | | |
|---|---|---|---|
| 4,005,571 | * | 2/1977 | Wolff . |
| 4,630,935 | * | 12/1986 | Zetter ...................................... 368/41 |
| 5,031,161 | * | 7/1991 | Kendrick ............................... 368/280 |
| 6,069,848 | * | 5/2000 | McDonald et al. ................... 368/107 |

OTHER PUBLICATIONS

Poynter, Douglas, Chapter 8, "Judging the Duration of Time Intervals: A Process of Remembering Segments of Experience", from *Time and Human Cognition A Life–Span Perspective*, Edited by Iris Levin and Dan Zakay, 1989.

Block, Richard A., Chapter 9, "Experiencing and Remembering Time: Affordances, Context, and Cognition", from *Time and Human Cognition A Life–Span Perspective*, Edited by Iris Levin and Dan Zakay, 1989.

Zakay, Dan, Chapter 10, "Subjective Time and Attentional Resource Allocation: An Integrated Model of Time Estimation", from *Time and Human Cognition A Life–Span Perspective*, Edited by Iris Levin and Dan Zakay, 1989.

* cited by examiner

*Primary Examiner*—Vit Miska
(74) *Attorney, Agent, or Firm*—McCormick, Paulding & Huber LLP

(57) ABSTRACT

A method and apparatus for comparing the perceived passage of time with the actual passage of time comprises a processor for determining at least one of an actual time of day and an actual period of time elapsed since an event. An interface communicates with the processor for entering at least one of a perceived time of day and a perceived period of time elapsed since an event. The processor calculates a deviation of a perceived passage of time relative to an actual passage of time. The deviation includes at least one of the difference between a perceived time of day and an actual time of day, and the difference between a perceived period of time elapsed since an event and an actual period of time elapsed since an event. An indicator is provided for communicating the deviation of a perceived passage of time relative to an actual passage of time.

18 Claims, 2 Drawing Sheets

METHOD AND APPARATUS FOR MEASURING SUBJECTIVE TIME

This invention relates generally to measuring the perceived passage of time, and more particularly relates to a method and apparatus for comparing the perceived passage of time with the actual passage of time to determine how efficiently one spends his or her time.

BACKGROUND OF THE INVENTION

The background for the present invention relates generally to the application of the concept of so-called "subjective time". Subjective or perceived time is defined as a time interval estimated not by mechanical, electronic, atomic or any other physical device but by a person based on his or her individual feeling and thought on how much time has passed since a certain moment.

The perceived estimation of the rate at which time passes is typically inaccurate. It is well known that time can "fly" or "crawl" to someone. Scientific data demonstrate that our accuracy in estimation of a long period of time (from several minutes to several hours) may vary (sometimes by an order of magnitude) depending on a number of reasons such as the type of activity exercised at a given interval, the number of events which have passed in the personal patterns of time perception, circadian and bio-rhythms, and environmental conditions. Such inaccuracy (i.e., the difference between actual or physical time and its perception) is, in itself, important and may be the key indicator of our peculiarity in time perception.

A number of well-known scientists such as Siffre, Aschoff, Waver, Block, Frigge, Campbell and others have developed theories about how the temporal judgment of long periods of time are made and based on the important fact that the perceived length of an interval of time depends at least partly on the volume and value of information being processed by someone during that interval.

One such explanation for the discrepancy between perceived and actual passage of time is a well-known theory of "two processors" developed by Thomas and Waver. This theory basically suggests that our attention at every particular moment is distributed or shared between two "brain processors"—the cognitive processor and a timer processor in such way that if we pay more attention to cognitive activity, the less attention we pay to timing itself, and as a result time appears to pass more quickly to us than it actually does. If we are paying more attention to the time itself and less attention to the activity we are engaging in time appears to pass more slowly to us than it actually does.

I have concluded from the foregoing that the degree of the "mistake" a human being makes in evaluating the time passing at any given interval indicates how deeply he or she is involved in a certain activity during the given interval of time. Such a variable may be called the "time delta".

For example, if the time delta of an individual at a certain period of time is higher than zero, it indicates that this person is "gaining" time; for this person "time flies". If the time delta of an individual at a certain period of time is less than zero, it indicates that this person is "losing time"; for this person "time crawls". If the time delta of an individual at a certain period of time equals zero, it means that this person is living "in time".

It is a general object of the present invention to provide a method and apparatus for processing information on the perceived passage of time to improve time management skills and thus lead to increased efficiency, productivity and enjoyment of one's activities.

SUMMARY OF THE INVENTION

In one aspect of the present invention, a method of comparing the perceived passage of time with the actual passage of time includes determining by a processor at least one of an actual time of day and an actual period of time elapsed since an event. At least one of a perceived time of day and a perceived period of time elapsed since an event is entered into the processor. A deviation of a perceived passage of time relative to an actual passage of time is calculated. The deviation includes at least one of the difference between a perceived time of day and an actual time of day, and the difference between a perceived period of time elapsed since an event and an actual period of time elapsed since an event. The deviation of a perceived passage of time relative to an actual passage of time is indicated, preferably by means of a digital display.

In another aspect of the present invention, an apparatus for comparing the perceived passage of time with the actual passage of time comprises means including a timer for determining at least one of an actual time of day and an actual period of time elapsed since an event. An interface communicates with the determining means for entering at least one of a perceived time of day and a perceived period of time elapsed since an event. The determining means includes means for calculating a deviation of a perceived passage of time relative to an actual passage of time. The deviation includes at least one of the difference between a perceived time of day and an actual time of day, and the difference between a perceived period of time elapsed since an event and an actual period of time elapsed since an event. Also provided is means for indicating the deviation of a perceived passage of time relative to an actual passage of time.

An advantage of the present invention is that the apparatus informs the user of various aspects of the user's perception of the speed time is passing so that the user can modify his or her activity patterns to make the most productive, efficient and enjoyable use of user's time.

Other advantages will be made apparent with reference to the following description and accompanying drawings.

DETAILED DESCRIPTION OF THE PREFERRED EMBODIMENT

Figure 1:
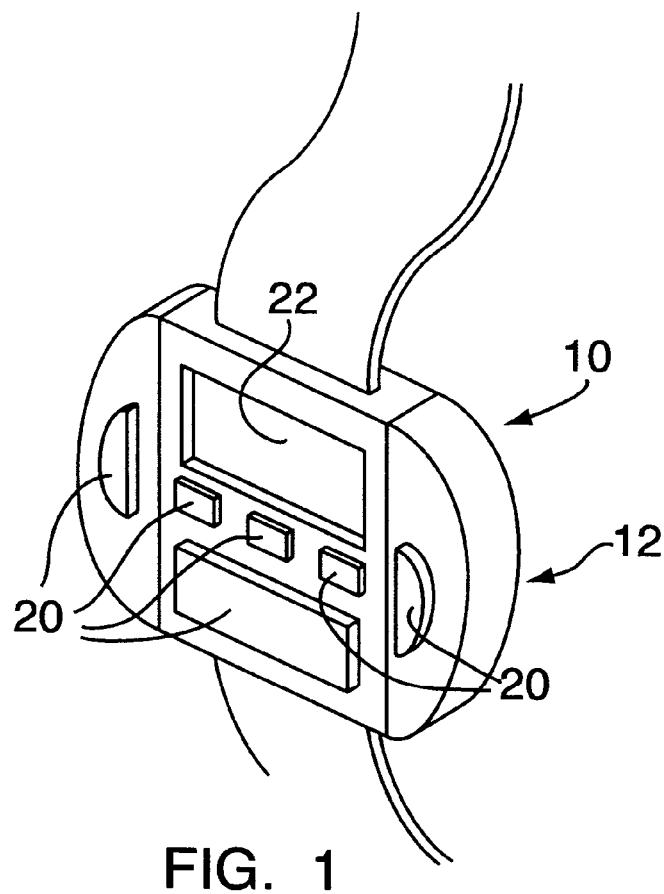
FIG. 1 is a schematic perspective view of an apparatus for processing information on the perceived passage of time in accordance with the present invention.
Figure 2:
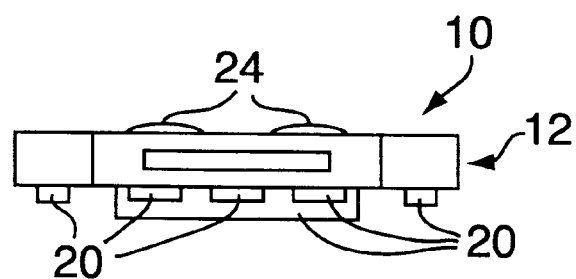
FIG. 2 is a schematic edge view of the apparatus of FIG. 1.
Figure 3:
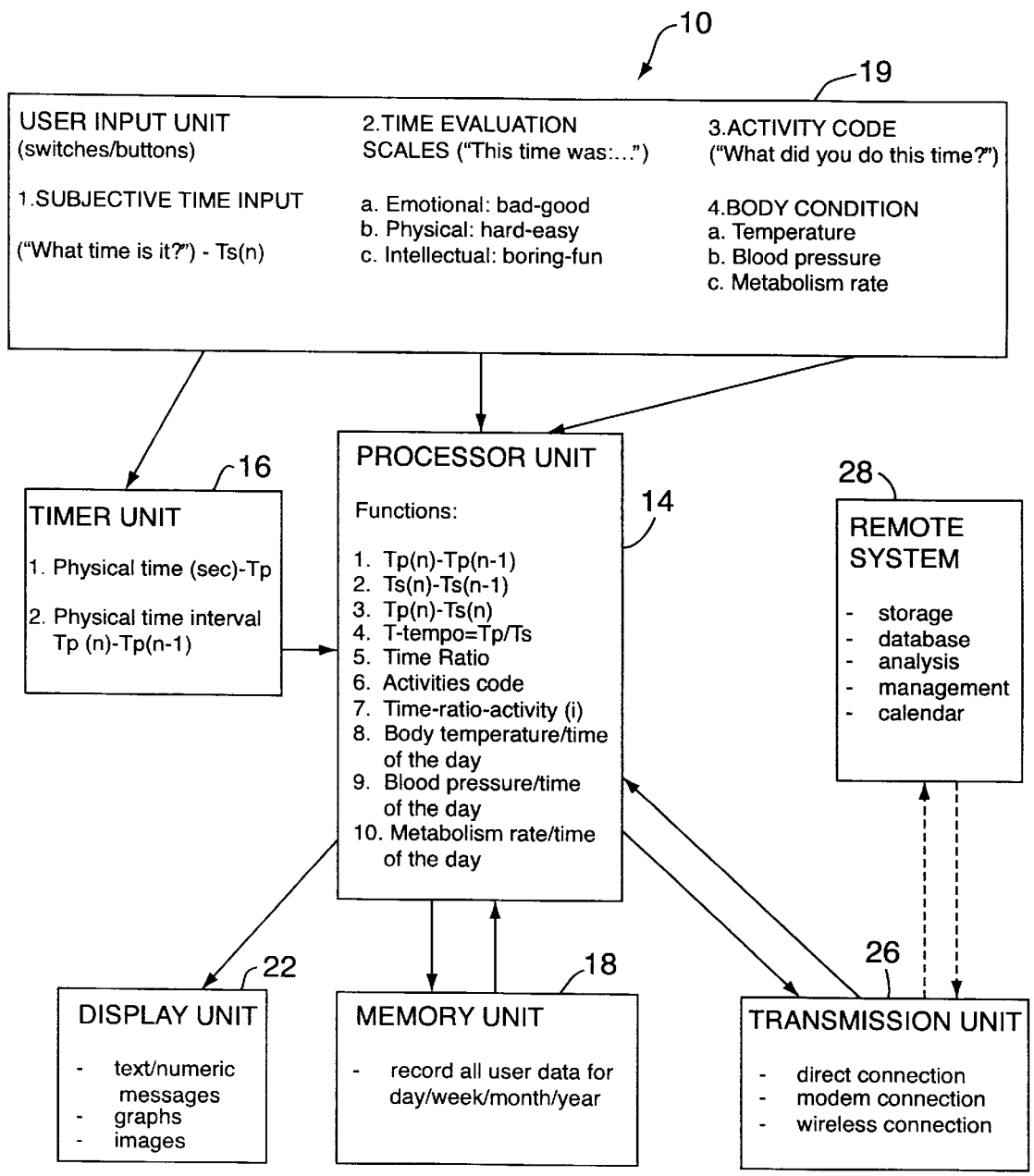
FIG. 3 is a schematic block diagram illustrating an example of various functions of components forming the apparatus of FIG. 1.

With reference to FIGS. 1–3, an apparatus for comparing the perceived passage of time with the actual passage of time in accordance with the present invention is generally designated by the reference number 10. Preferably as shown in FIGS. 1 and 2, the apparatus 10 is a small, inexpensive, wearable device similar in form to a wristwatch, but alternatively may take on other forms such as a stand-alone device or incorporation in a stand-alone device. For example, the apparatus may be incorporated in desk and mobile phones, digital organizers, toys, calculators, audio recorders, CD players, portable radios, clocks, personal computers, laptops and personal digital assistants. Further, the apparatus 10 may be a part of a central storage and processing unit that is accessible through the LAN or the Internet. The apparatus 10 may be manufactured based on mechanical devices, discrete electronic components, or microprocessor technology. The apparatus 10 will be described by way of example as comprising a microprocessor and/or small electronic components.

The apparatus 10 provides a user with valuable data as "losses" and "gains of time", intensity of activity during a certain period, individual time spending patterns (i.e. with optimum, maximum and minimum productivity indications), biological, physiological and psychological personal rhythmic patterns, as well as the precise measurement and calculation of the intellectual, emotional and physical individual characteristics. The present invention enables the user to easily predict his or her psychological conditions, periods of crises and most productive life periods in order to improve the user's time management skills. Improved time management skills lead to increased efficiency, productivity and enjoyment of the user's activities whether they be work related or recreational.

The apparatus 10 includes a housing 12, means for determining time-related functions such as the time of day and an actual period of time elapsed since an event (i.e., a timer function). As shown in FIG. 3, the determining means includes a processor 14, a timer 16 and memory 18 which are all preferably in the form of integrated circuits or other electronic components. Preferably, the timer 16 and the memory 18 are part of the processor 14, but alternatively may be separate components. The timer 16 measures physical or actual time durations as well as time interval estimates (i.e., subjective or perceived time durations) entered by the user. The memory 18 keeps record of all data from an input interface 19 and the processor 14, and stores personal time records for certain periods of time such as, for example, days, months and years. The input interface 19 supported on the housing 12 includes one or more switches or buttons 20, 20 for entering information into the processor 14. An indicator or display 22 communicates information from the processor 14 to the user. The display 22 may show the user data in the form of text/numeric messages, graphs and graphical images. The input interface 19 may also include a plurality of sensors 24,24 for receiving physical information of a user including, for example, body temperature, blood pressure, pulse rate and metabolism. A transmission unit 26 (see FIG. 3) may permit the transmission of digital information from the processor 14 to a remote system 28 such as a storage database in a personal computer, network or remote server by wire (direct) connection, modem or wireless protocols for later storage, manipulation and analysis.

The plurality of buttons 20, 20 forming part of the input interface 19 permit the user to submit, among other things, his or her subjective time interval estimation. The user periodically, or at predetermined time intervals, or at the beginning and at the end of an activity, submits the time he or she thinks it is at that point, or the time interval he or she thinks has passed since his or her last submission.

The input interface 19 also permits the user to mark a certain period of time by entering into the processor 14 what type of activities he or she was performing during this period of time, as well as index or grade such an activity on an intellectual, emotional and physical scale. The scale may be any type of ranking system such as, for example, a ranking system employing the integers from 0 to 10. Using the integer ranking system by way of example, as an emotional indicator the scale of integers 0to 10 may represent a range of emotions from bad to good; as a physical indicator, the scale of integers from 0 to 10 may represent a range from hard to easy, and as an intellectual indicator, the integers from 0 to 10 may represent a range from boring to fun. The buttons 20, 20 of the input interface 19 may provide means for answering preprogrammed questions shown on the display 22 about issues related to the user's experience at a given time interval.

As will be explained more fully below, the processor 14 compares and calculates the difference between the physical or actual time and the subjective or perceived time intervals of the user. The processor 14 manipulates the actual and perceived time information for providing relevant information to the display 22 to inform the user as to how efficient the user is spending his or her time. One may learn from the apparatus 10 that he or she is more efficient at certain times of day, or is more productive in certain activities. Such information is useful for changing one's activity patterns to make more efficient, productive and enjoyable use of one's time.

Turning now to FIG. 3, the function of the apparatus 10 will be described in greater detail. The processor 14 may perform several tasks and calculations, some of which are shown in FIG. 3 and some of which are now described by way of example.

1) Keep track of actual, physical time intervals in units such as seconds, minutes, hours, days, months and years by means of the following calculation:

$$Tp=Tp(n)-Tp(n-1),$$

Where Tp=physical or actual time interval, Tp (n)=actual time at moment n, and Tp (n−1)=actual time at a previous moment (n−1).

2) Determine subjective or perceived (psychological, individual, "inner") time intervals of elapsed time in "subjective minutes", "subjective hours", "subjective days", etc. by means of the following calculation:

$$Ts=Ts(n)=Ts(n-1),$$

Where Ts=subjective time intervals, Ts (n)=subjective time at moment n, and Ts (n−1)=subjective time at a previous moment (n−1).

3) Compare subjective and actual time in order to provide a measure of human experience of time. The difference between actual time and subjective time (time delta or TΔ) is a human scale of duration, and is calculated as follows:

$$T\Delta(n)=Tp(n)-Ts(n),$$

Where Tp (n)=physical time of interval n and Ts (n)= subjective time of the same interval.

4) Determine a personal time tempo (T-tempo or Tt). A higher value of Tt means the more "subjective minutes" a user can "fit" in an actual minute. In other words, Tt is "the speed" of personal life, where the higher the value of Tt, the more productive, efficient and enjoyable is one's use of time. Personal time tempo is calculated as follows:

$$Tt(n)=Tp(n)/Ts(n).$$

First example: suppose Ts=1 hour and Tp=1 hour, then Tt=1. This means that for each subjective minute, a user fits exactly one physical minute.

Second example: suppose a user estimates that duration of a certain time interval is 1 hour (Ts=1 hour), but the physical time interval is only 30 minutes (Tp=½ hour). This means that in each subjective minute during this interval the user actually fits only half of a physical minute. Hence the user's "tempo" or "speed of living" is twice as slow as in the previous example, i.e., Tt =½. In this example "time crawls" such that the user generally is not making productive use of time.

Third example: suppose a user estimates that an interval is 1 hour (Ts=1 hour), but the physical interval is 2 hours (Tp=2 hours). This means that during this particular interval the user fits in each subjective minute two physical minutes.

Hence the user's T-tempo during this interval (i.e., "time speed", "how fast user is moving in time") is twice as fast as in the first example (i.e., Tt=2). In this example "time flies" such that the user is making highly productive use of time.

5) Calculate a personal time ratio (T-ratio or Tr). Tr is a mathematical manipulation of subjective time (Ts) and physical time (Tp) which gives information as to not only the subjective speed of the passage of time, but also what type of activity causes time to pass at a given speed.

For example, a user of the apparatus 10 believes that while performing activity "A" user feels that time usually flies, and while performing activity "B" user feels time usually goes slowly. By systematic measurements of Ts's and Tp's and calculating time tempos during such activities using the apparatus 10 of the present invention, the user can learn that different activities have more or less constant values of corresponding time tempos. For example, activity "A" (say—playing chess) for a user may have an average Tt equal to 2 and an activity "B" (say—driving a car) may have an average Tt equal to ½. From this information the user can create a list of pairs: "activity (i)—Tt (i), where "i" indicates a type of activity. This average value of time tempos for a given activity "i" can be stored in the apparatus 10, and is defined as the time ratio Tr (i) of activity "i".

According to the above-mentioned theory of two processors, the time ratio Tr of a certain activity is an indicator of the level of personal involvement (engagement) in such activity. Using the apparatus 10 to measure values of Tr (i) for each activity enables the user to evaluate which activity engages the user more (i.e., makes "time fly") or less (makes "time crawl") and hence, the user will be able to predict how he or she will spend time doing one activity or another.

For example, if a user employing the apparatus 10 determines that the time ratio of an activity "A" is greater than the time ratio of an activity "B" (i.e., Tr (a)>Tr (b)), the user will learn that activity "A" is generally more productive, creative and enjoyable relative to activity "B".

Thus, different types of activities may be ranked by the apparatus 10 according to relative productivity. This ranking may be employed to normalize and compare perception patterns of individuals.

It will be possible to employ the apparatus 10 to test different users by comparing their T-ratios of the same activity. For example, to determine who is "the best" in programming, several candidates may be asked to solve the same programming task and then to record their time interval estimates in the apparatus 10 for comparison with the actual elapsed time interval. The user who has the highest T-ratio may be considered the person whom the process "programming" is more productive, creative and enjoyable relative to the other users tested.

By collecting a user's data (Tp and Ts) in the apparatus 10 and by comparing and using the apparatus to manipulate this data in many different meaningful mathematical and statistical ways, different characteristics of a user's patterns of spending time can be determined. Thus, the user of the apparatus 10 can emotionally interact with his or her own subjective time patterns so that it has a uniquely personal relevance to the user.

The operation of the apparatus 10 will now be described by way of example. The user enters via the buttons 20, 20 of the input interface 19 input data regarding the user's estimation of the length of a given time interval that has elapsed since a previous entry or from a known time of day. The user may also enter via the buttons 20, 20 a list of activities performed during the time interval. Further, the user may index or grade such activity via the buttons 20, 20 on an intellectual, emotional and physical scale. As mentioned previously, the scale may be any type of ranking system such as, for example, a ranking system employing the integers from 0 to 10. Using the integer ranking system by way of example, as an emotional indicator scale of integers from 0 to 10 may represent a range of emotions from bad to good; as a physical indicator, the scale of integers from 0 to 10 may represent a range from hard to easy, and as an intellectual indicator, the integers from 0 to 10 may represent a range from boring to fun.

Meanwhile, the processor 14 measures by means of the timer 16 the actual time intervals between the user's inputs or the known time of day. The apparatus 10 may also receive input data from the one or more sensors 24, 24 of the input interface 19 on various physical attributes such as body temperature, heart rate, blood pressure, and metabolism during the time interval. The received data entered by the user and received by the sensors 24, 24 are stored in the memory 18 and associated with the time of day and actual time intervals determined by the timer 16. The processor 14 generates the parameters of the user's current time experience state and psychological condition (bio-psychological rhythms and patterns), and the user's past time experience states and psychological conditions. The data and statistical information is transferred to the display 22 in the form of text/number messages, graphs and images. For example, the processor 14 may calculate and transfer to the display 22 such information as the actual time of day, an actual time interval Tp elapsed since a predetermined time of day or previous time entry by the user, a subjective or perceived time interval Ts elapsed since the predetermined time of day or previous entry, a time-tempo, and a T-ratio. The processor 14 may also communicate with the remote system 28 in order to pass and retrieve data. The apparatus 10 may also be acted upon by commands executed by the remote system 28.

Although the present invention has been shown and described in a preferred embodiment for use by an individual who desires to monitor his or her lifestyle and his or her progress toward the achievement of a set goal, it may also be used by a group of individuals who share a common set of goals. For example, co-workers, members of one production or sport team, and so on, may use this system for re-evaluating their meeting time, scheduling group activities based on each member's best time option. This system may also be used by managers of groups of shift workers, to optimize the group schedule, as well as for people who have to travel among time zones. Further, other manipulations of Tp and Ts may be made to produce meaningful information to the user without departing from the scope of the present invention. Accordingly, the present invention has been shown and described in a preferred embodiment by way of illustration rather than limitation.

What is claimed is:

1. A method of comparing the perceived passage of time with the actual passage of time, comprising the steps of:

determining by a processor at least one of an actual time of day and an actual period of time elapsed since an event;

entering into the processor at least one of a perceived time of day and a perceived period of time elapsed since an event;

calculating a deviation of a perceived passage of time relative to an actual passage of time, the deviation including at least one of the difference between a perceived time of day and an actual time of day, and the difference between a perceived period of time elapsed since an event and an actual period of time elapsed since an event; and indicating the deviation of a perceived passage of time relative to an actual passage of time.

2. A method as defined in claim 1, further including the step of monitoring at least one of a user's pulse rate, body temperature, blood pressure and characteristics of metabolism.

3. A method as defined in claim 1, further including the step of entering into the processor the type of activities that a user is performing.

4. A method as defined in claim 1, further including the step of entering into the processor information on the subjective dispositions of a user of at least one of an intellectual, emotional and physical scale.

5. A method as defined in claim 4, wherein the intellectual scale employs a rank representing a range from boring to fun, the emotional scale employs a rank representing a range from bad to good, and the physical scale employs a rank representing a range from hard to easy.

6. A method as defined in claim 1, further including the step of calculating a time tempo or perceived pace of time defined as (an actual period of time elapsed since an event)/(a perceived period of time elapsed since an event).

7. A method as defined in claim 6, further including the step of calculating a level of personal involvement of a user in a given activity defined as the average time tempo associated with an activity.

8. An apparatus for comparing the perceived passage of time with the actual passage of time, the apparatus comprising:

means for determining at least one of an actual time of day and an actual period of time elapsed since an event;

an interface communicating with the determining means for entering at least one of a perceived time of day and a perceived period of time elapsed since an event, the determining means including means for calculating a deviation of a perceived passage of time relative to an actual passage of time, the deviation including at least one of the difference between a perceived time of day and an actual time of day, and the difference between a perceived period of time elapsed since an event and an actual period of time elapsed since an event; and means for indicating the deviation of a perceived passage of time relative to an actual passage of time.

9. An apparatus as defined in claim 8, wherein the determining means includes a processor.

10. An apparatus as defined in claim 8, further including a housing in the form of a wristwatch for accommodating the determining means, and wherein the interface is located on the housing.

11. An apparatus as defined in claim 10, wherein the interface includes at least one button for entering the at least one of a perceived time of day and a perceived period of time elapsed since an event.

12. An apparatus as defined in claim 10, wherein the indicating means includes a digital display.

13. An apparatus as defined in claim 8, further including means for monitoring at least one of a user's pulse rate, body temperature, blood pressure and characteristics of metabolism.

14. An apparatus as defined in claim 8, further including means for entering the type of activities that a user is performing.

15. An apparatus as defined in claim 8, further including means for entering the subjective dispositions of the user of at least one of an intellectual, emotional and physical scale.

16. An apparatus as defined in claim 15, wherein the intellectual scale employs a rank representing a range from boring to fun, the emotional scale employs a rank representing a range from bad to good, and the physical scale employs a rank representing a range from hard to easy.

17. An apparatus as defined in claim 8, wherein the determining means includes means for calculating a time tempo or perceived pace of time defined as (an actual period of time elapsed since an event)/(a perceived period of time elapsed since an event).

18. An apparatus as defined in claim 17, wherein the determining means includes means for calculating a level of personal involvement of a user in a given activity defined as the average time tempo associated with an activity.

* * * * *